(12) United States Patent
Berrier et al.

(10) Patent No.: US 11,471,177 B2
(45) Date of Patent: Oct. 18, 2022

(54) CLAMPING FORCEPS DEVICE

(71) Applicant: Critical Care Excellence, LLC, Goldsboro, NC (US)

(72) Inventors: Michael Carr Berrier, Goldsboro, NC (US); Jared Little, Durham, NC (US)

(73) Assignee: CRITICAL CARE EXCELLENCE, LLC, Goldsboro, NC (US)

( * ) Notice: Subject to any disclaimer, the term of this patent is extended or adjusted under 35 U.S.C. 154(b) by 520 days.

(21) Appl. No.: 16/699,816

(22) Filed: Dec. 2, 2019

(65) Prior Publication Data

US 2021/0161548 A1 Jun. 3, 2021

(51) Int. Cl.
| | | |
|---|---|---|
| *A61B 17/28* | (2006.01) | |
| *A61M 16/08* | (2006.01) | |
| *A61M 16/04* | (2006.01) | |
| *A61B 17/00* | (2006.01) | |

(52) U.S. Cl.
CPC ...... *A61B 17/2816* (2013.01); *A61B 17/2841* (2013.01); *A61M 16/0463* (2013.01); *A61M 16/0465* (2013.01); *A61M 16/0875* (2013.01); *A61B 2017/00353* (2013.01); *A61B 2017/2808* (2013.01); *A61B 2017/2837* (2013.01)

(58) Field of Classification Search
CPC ..... A61B 17/00; A61B 17/28; A61B 17/2841; A61B 17/30; A61B 2017/2808; A61B 2017/305; B25G 1/10; B25B 23/16; B25B 7/00; B25B 7/22; B26B 13/12; B26B 13/22; B25F 1/003; B25F 1/04; A61M 16/0688; A61M 16/0465; A61M 16/0875; A61M 16/04; A61M 16/0402; A61M 16/0463; A61M 16/0472; A61M 16/08; A61C 3/14

See application file for complete search history.

(56) References Cited

U.S. PATENT DOCUMENTS

| | | | | |
|---|---|---|---|---|
| D285,166 S | * | 8/1986 | Lee | ................................... D8/57 |
| 5,997,566 A | * | 12/1999 | Tobin | .................... A61B 17/282 |
| | | | | 606/205 |
| 7,438,717 B2 | * | 10/2008 | Tylke | ...................... A61B 17/28 |
| | | | | 606/205 |
| 8,668,699 B2 | * | 3/2014 | Thomas | .............. A61B 17/8863 |
| | | | | 606/86 R |
| 2006/0271102 A1 | * | 11/2006 | Bosshard | ........... A61B 17/2812 |
| | | | | 606/205 |
| 2014/0324000 A1 | * | 10/2014 | Hill | ........................ A61M 27/00 |
| | | | | 604/328 |
| 2015/0217462 A1 | * | 8/2015 | Cotter | ...................... A01G 3/02 |
| | | | | 30/123 |

FOREIGN PATENT DOCUMENTS

WO WO-2017205376 A1 * 11/2017 ............... B25B 7/08

* cited by examiner

*Primary Examiner* — Sarah W Aleman
(74) *Attorney, Agent, or Firm* — NK Patent Law (57) ABSTRACT

Clamping forceps device includes two clamps in pivotal connection to one another and each having an operator end for being operated by a health care provider. The device also includes an extension extending aft of the operator end of each clamp, the extension forming a space therebetween sized to form a disconnecting wedge mechanism for separating a tube from a patient tube connector. Each extension defines a ramped surface increasing in thickness moving from an extension tip towards the operator end.

2 Claims, 7 Drawing Sheets

CLAMPING FORCEPS DEVICE

TECHNICAL FIELD

This invention relates generally to the field of healthcare and specifically to a clamping forceps device with a built-in disconnecting wedge mechanism for separating a fluid supply tube from a patient tube connector.

BACKGROUND

Tracheal intubation is one of the most common procedures performed in an operating room and during transit in an ambulance. The procedure involves the introduction of a plastic endotracheal tube into the patient's trachea to create an open channel for air and gas to flow. The endotracheal tube is a flexible plastic tube that is placed through the mouth into the trachea (windpipe) to help a patient breathe. A patient tube connector located at the end of the endotracheal tube then connects to a tube in fluid communication with a source of gas or fluid such as, for example, an oxygen cylinder of an ambulance, to deliver oxygen to the lungs. When the ambulance reaches an emergency care hospital and the patient is ready to be transferred via a stretcher, for example, a medical professional needs to disconnect the tube supplying oxygen from the patient tube connector of the endotracheal tube. Similarly, while the patient is in hospital, there is often a need to disconnect the tube supplying gas from the patient tube connector of the endotracheal tube in order for the patient tube connector to be connected to a new or different source of gas.

Often it can be difficult to disconnect the patient tube connector from an end of the oxygen supply tube, and a wedge mechanism may be needed to pry between the patient tube connector and an end of the oxygen supply tube to disconnect the endotracheal tube from the oxygen supply tube. However, the wedge mechanism may not be readily available or a properly sized wedge mechanism may not be readily available, both of which can lead to unnecessary delay caused in the transfer of the patient from the ambulance to the operating room. Further, an improperly sized wedge mechanism can result in discomfort to the patient as the fluid or gas supply tube is being disconnected from the patient tube connector.

It would be desirable to provide a wedge mechanism that is easily accessible to medical professionals and which cannot be easily misplaced such that the unnecessary delay that may associated with disconnecting the patient tube connector from an end of the oxygen supply tube is avoided.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

In accordance with the purposes of the disclosed devices and methods, as embodied and broadly described herein, the disclosed subject matter relates to devices and methods of use thereof. Additional advantages of the disclosed devices and methods will be set forth in part in the description, which follows, and in part will be obvious from the description. The advantages of the disclosed devices and methods will be realized and attained by means of the elements and combinations particularly pointed out in the appended claims. It is to be understood that both the foregoing general description and the following detailed description are exemplary and explanatory only and are not restrictive of the disclosed compositions, as claimed.

The details of one or more embodiments of the invention are set forth in the accompanying drawings and the description below. Other features, objects, and advantages of the invention will be apparent from the description and drawings, and from the claims.

Disclosed herein is a device for clamping forceps device. According to various embodiments, the device includes two clamps in pivotal connection to one another and each having an operator end for being operated by a health care provider. The device also includes an extension extending aft of the operator end of each clamp, the extension forming a space therebetween sized to form a disconnecting wedge mechanism for separating a tube from a patient tube connector, wherein each extension defines a ramped surface increasing in thickness moving from an extension tip towards the operator end.

According to one or more embodiments, each clamp further comprises a mutually engaging ratchet interlock extending towards the other clamp.

According to one or more embodiments, the extension tip forms a wedge for insertion between an end connection of the tube and the patient tube connector.

According to one or more embodiments, the disconnecting wedge mechanism defines an approximate u-shape.

According to one or more embodiments, each extension incudes an elevated ridge at a side facing the other extension, wherein the elevated ridge is configured for engaging the patient tube connector when the patient tube connector is being separated from the tube.

According to one or more embodiments, the clamps are configured for pivoting about a hinge when moving from an occlusion position for occluding a tube supplying a fluid to a patient to an open position.

According to one or more embodiments, the disconnecting wedge mechanism is formed in the closed position.

According to one or more embodiments, the mutually engaging ratchet interlock of each clamp engages the other clamp when the clamps are in a closed position.

According to one or more embodiments, the clamps comprise a rigid thermoplastic material.

According to one or more embodiments, the clamps comprise a stainless steel.

According to one or more embodiments, the patient tube connector is configured for coupling to a ventilator tube inserted in a mouth or nose of a person.

Disclosed herein is a method of using a clamping forceps device. According to various embodiment, the method includes providing a clamping forceps device. The clamping forceps device includes two clamps in pivotal connection to one another and each having an operator end for being operated by a health care provider; and, an extension extending aft of the operator end of each clamp, the extension forming a space therebetween sized to form a disconnecting wedge mechanism for separating a tube from a patient tube connector, wherein each extension defines a ramped surface increasing in thickness moving from an extension tip towards the operator end. The method further includes inserting an extension tip of each extension between a tube end and the patient tube connector. The method also includes separating the tube end from the patient tube connector.

According to one or more embodiments, each extension incudes an elevated ridge at a side facing the other extension, wherein the method further comprises engaging a separated patient tube connector with elevated ridge.

DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

DETAILED DESCRIPTION

The following description and drawings are illustrative and are not to be construed as limiting. Numerous specific details are described to provide a thorough understanding of the disclosure. However, in certain instances, well-known or conventional details are not described in order to avoid obscuring the description. References to "one embodiment" or "an embodiment" in the present disclosure can be, but not necessarily are, references to the same embodiment and such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and is not intended to further limit the scope and meaning of the disclosure or of any exemplified term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms herein have the same meaning as commonly understood by one of ordinary skill in the art to which this disclosure pertains. In the case of conflict, the present document, including definitions, will control.

Embodiments of the presently disclosed subject matter provide for clamping forceps that advantageously includes a built-in wedge mechanism that can assist in expeditiously disconnecting the patient tube connector from an end of the oxygen supply tube. Embodiments of the presently disclosed subject matter accordingly provide for a wedge mechanism that is easily accessible to medical professionals such that the unnecessary delay that may associated with disconnecting the patient tube connector from an end of the oxygen supply tube is avoided.

Figure 1:
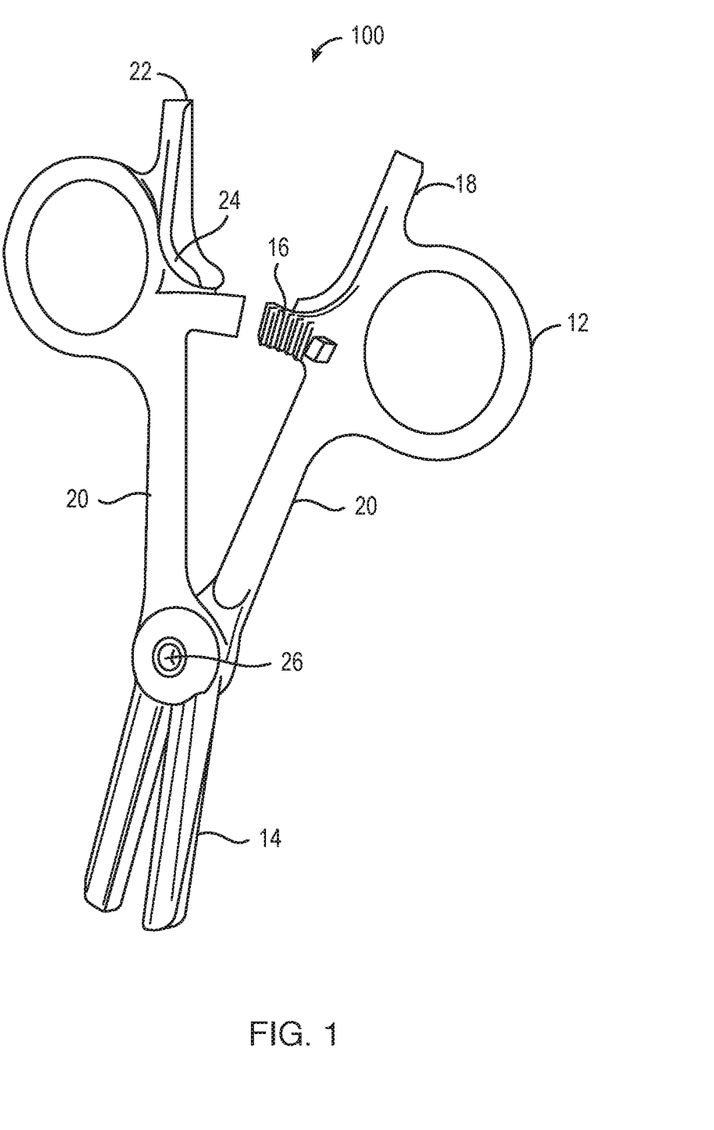
FIG. 1 is a front perspective view of a clamping forceps device, according to one or more embodiments of the presently disclosed subject matter.
Figure 2:
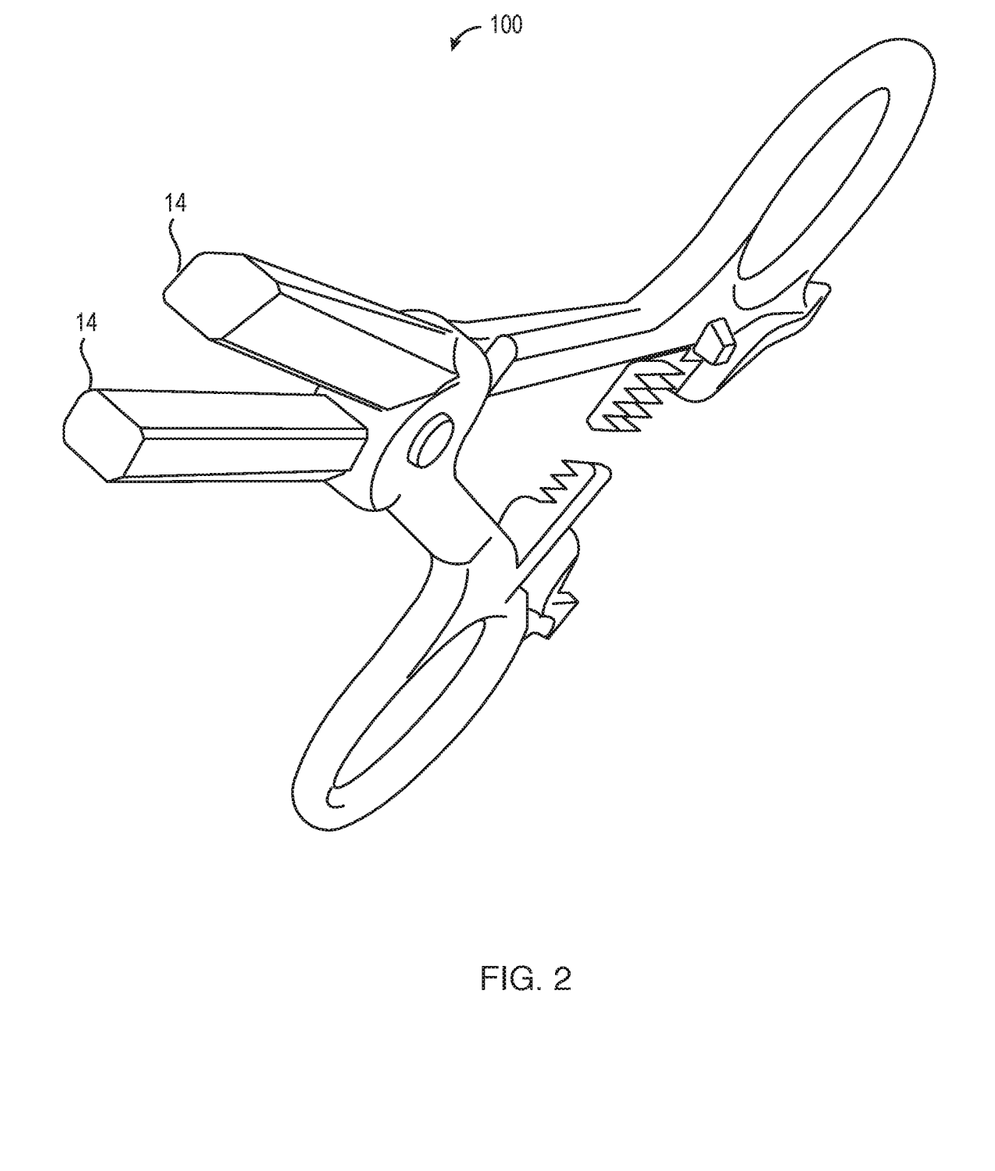
FIG. 2 is a bottom-front perspective view of a clamping forceps device, according to one or more embodiments of the presently disclosed subject matter.
Figure 3:
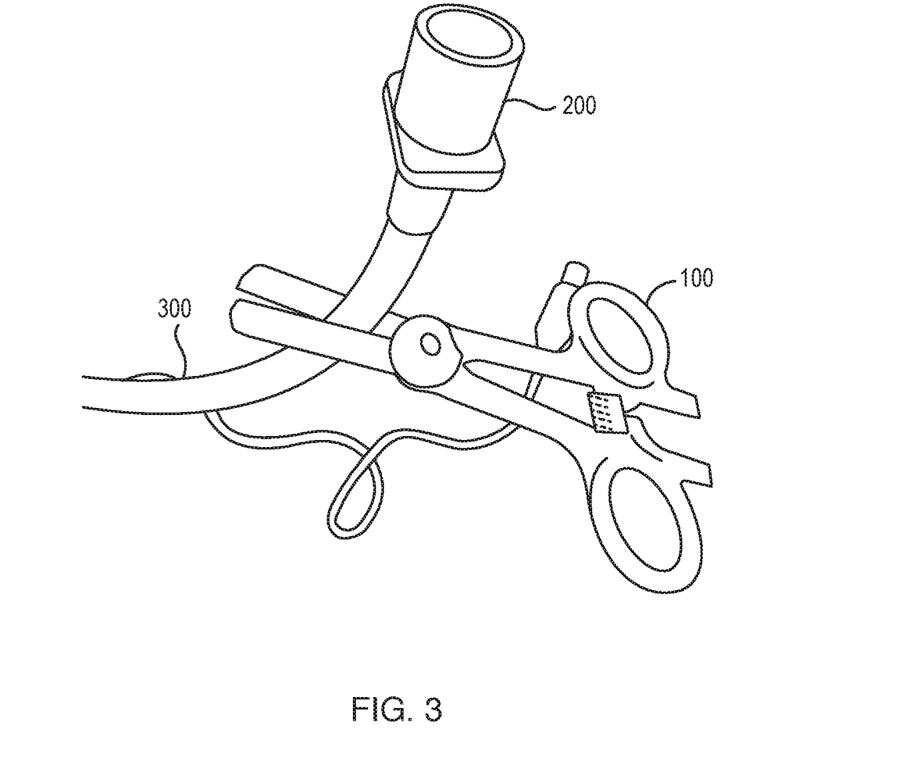
FIG. 3 is a side perspective view of a clamping forceps device occluding a tube, according to one or more embodiments of the presently disclosed subject matter.
Figure 4:
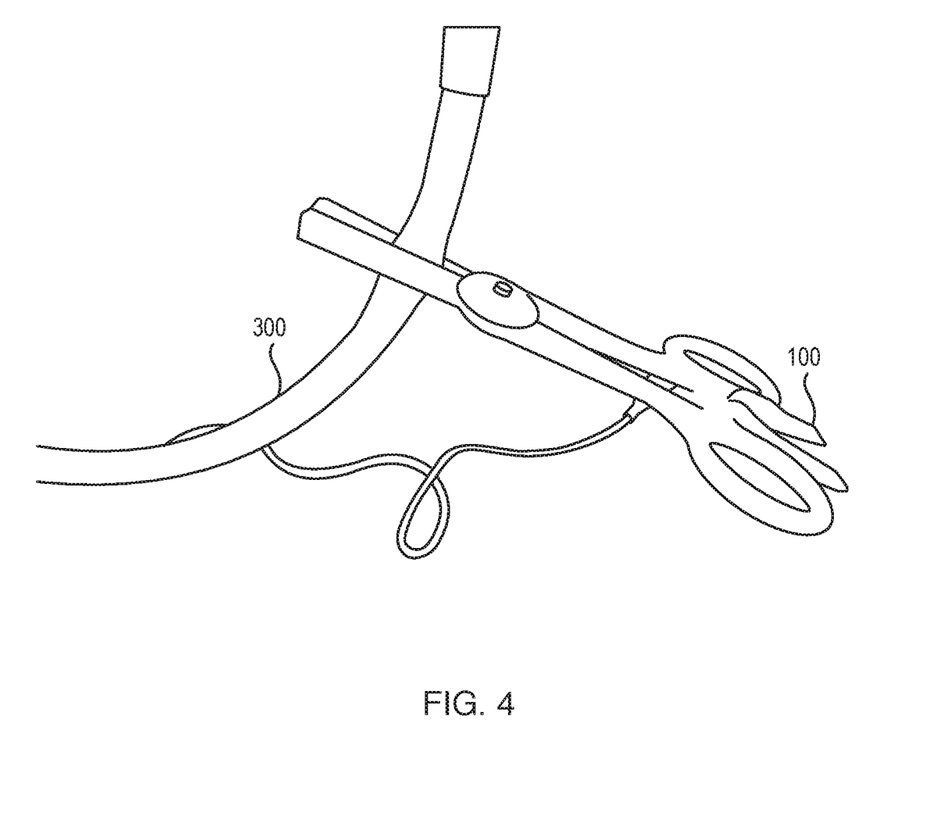
FIG. 4 is a side perspective view of a clamping forceps device occluding a tube, according to one or more embodiments of the presently disclosed subject matter.

Referring to FIGS. 1 through 6, embodiments of the presently disclosed subject matter include a pair of clamping forceps. In at least one embodiment, as shown, for example, in FIG. 1, clamping forceps 100 includes two clamps 20 in pivotal connection to one another with each clamp 20 having an operator end 12 for being operated by a health care provider and a clamping end for occluding flow of a fluid through a tube (occlusion of a tube is shown, for example, in FIGS. 3 and 4). Each clamp 20 further includes an extension 18 extending aft of the operator end 12 of each clamp 20. Extensions 18 form a space therebetween sized to form a disconnecting wedge mechanism for separating a tube such as tube 300 from a patient tube connector 200. Separation of a tube such as tube 300 from a patient tube connector 200 using the disconnecting wedge mechanism is illustrated, for example, in FIGS. 6 and 7. As shown in FIG. 1, each extension 18 defines a ramped surface that increases in thickness moving from an extension tip 22 (labeled in FIG. 1) towards operator end 12. In at least one embodiment, patient tube connector 200 is configured for coupling to a ventilator tube or a tracheal tube inserted in a mouth or nose of a person.

As shown in FIG. 1, each clamp 20 further includes a mutually engaging ratchet interlock 16 extending towards the other clamp. In use, as shown, for example, in FIG. 3, when medical professional intends to occlude a tube supplying a fluid, the medical professional works the operating end 12 to move clamping ends 14 towards each other to a closed (or occluded) position in order to occlude a tube such tube 300 to reduce or eliminate the flow of fluid or gas therethrough. As the clamp ends 14 are forced towards each other by the medical professional, the interlocks on each ratchet interlock 16 begin to ratchet towards each other. When the medical professional completes the clamping operation whereby the tube has been adequately occluded by clamp ends 14, and the medical professional starts to release the medical professional's hands from the operator end, the interlocking of the ratchet interlock 16 operates to prevent the clamps 20 from moving out of the closed position, thereby securely retaining clamping ends 14 in place to maintain the clamping forceps 100 in an occluded or closed position even after the medical professional releases the force applied at the operator ends. Accordingly, in various embodiments, the ratchet interlock 16 of each clamp 20 mutually engages the ratchet interlock 16 of the other clamp 20 when the clamps of clamping forceps 100 are in a closed position.

Figure 5:
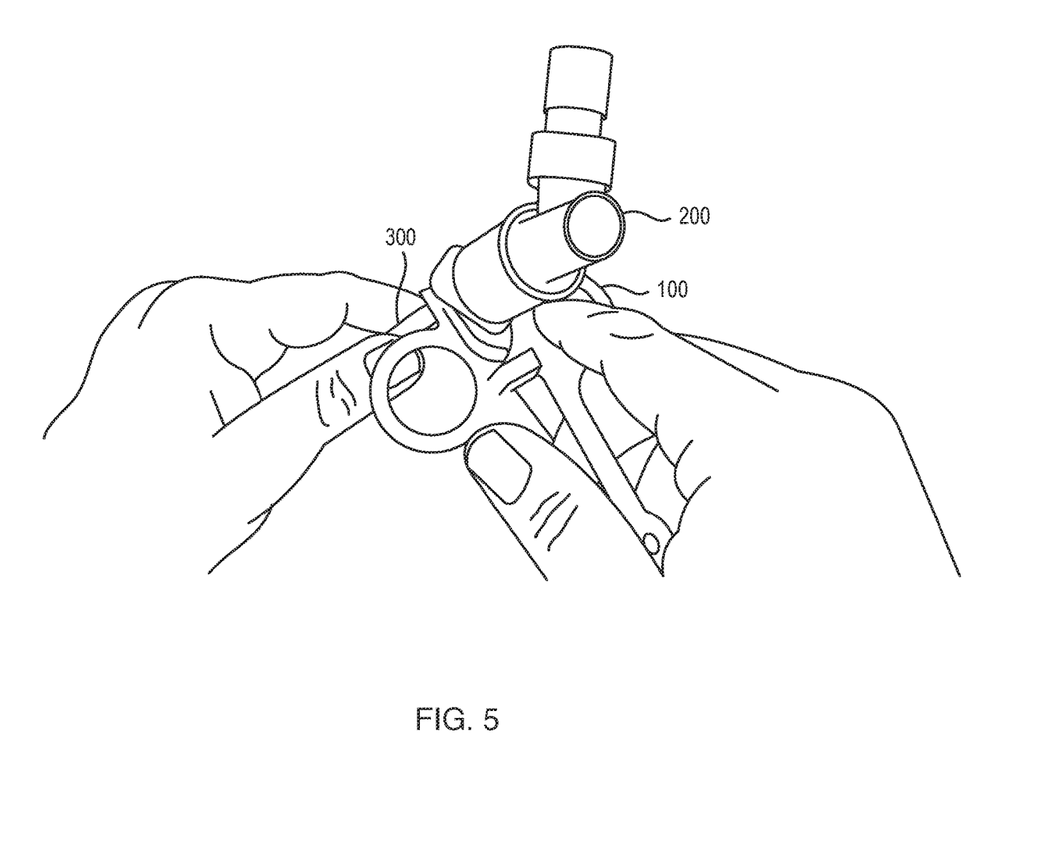
FIG. 5 is a perspective view of a clamping forceps device in the process of being used to separate a patient tube connector from a tube end, according to one or more embodiments of the presently disclosed subject matter.

In at least one embodiment, extension tip 22 operates to form part of a wedge mechanism for insertion between an end connection of a tube such as tube end 310 (see FIG. 6) of tube 300 and the tube connector 200. As shown in FIG. 5, the disconnecting wedge mechanism formed by extensions 18 defines an approximate u-shape in at least one embodiment. As shown in FIG. 5, this approximately u-shaped disconnecting wedge mechanism can advantageously be used to separate patient tube connector 200 from tube end 310 by starting to insert wedge extension tip 22 at the point or junction at which patient tube connector 200 contacts with tube end 310. After the disconnecting wedge mechanism is sufficiently inserted and the patient tube connector 200 is completely separated from tube 300, u-shaped disconnecting wedge mechanism can advantageously operate to hold or support patient tube connector 200. To facilitate the holding or supporting of patient tube connector 200 during and after the separation of patient tube connector 200 from tube 300, each extension 18 includes an elevated ridge such as ridge 24 at the side facing the other extension (see FIG. 1), whereby ridge 24 operates to engage patient tube connector 200 when patient tube connector 200 is being separated from tube 300, and to continue to engage patient tube connect 200 after it is separated from tube 300.

As shown, for example, in FIG. 1, clamps 20 are configured for pivoting about a hinge such as hinge 26 when moving from an occlusion position (for occluding a tube supplying a fluid to a patient such as tube 300) to an open position wherein clamps 20 are not contacting tube 300.

As noted earlier, according to at least one embodiment, clamping forceps 100 is configured for forming the approximately u-shape of the disconnecting wedge mechanism when the clamps are in the closed position (or the occluded position). However, this is not a requirement. For example, the clamping forceps 100 can be configured to form the disconnecting wedge mechanism even when the clamps are in an open position, for example, so that clamping forceps 100 can operate to engage and separate a patient tube connector having a relatively large diameter or cross section even when the clamps are in the open position.

The clamping forceps as described herein can be formed of any suitable materials as understood by persons of skill in the relevant art. For example, in one embodiment, clamping forceps can be formed of a plastic material such as, for example, a rigid thermoplastic material. In another embodiment, clamping forceps can be formed of a metallic substance such as, for example, stainless steel.

Figure 6:
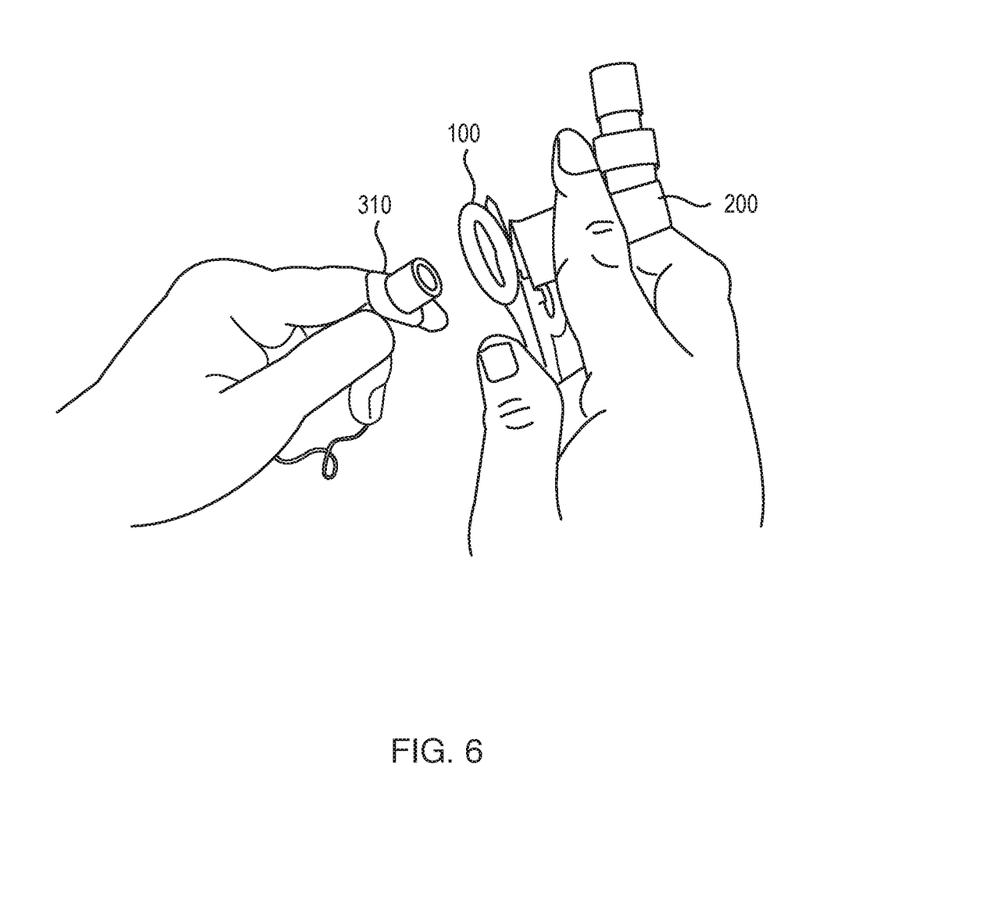
FIG. 6 is a perspective view of the clamping forceps device with the patient tube connector having been separated from a tube end, according to one or more embodiments of the presently disclosed subject matter.

As illustrated in FIGS. 5 and 6, a method of using a clamping forceps device as disclosed herein includes providing clamping forceps device 100 for separating a patient tube connector from a tube end. FIG. 5 is a perspective view of a clamping forceps device in the process of removing a patient tube connector, according to one or more embodiments of the presently disclosed subject matter. FIG. 6 is a perspective view of the clamping forceps device with the patient tube connector having been removed, according to one or more embodiments of the presently disclosed subject matter. The method includes inserting an extension tip 22 of each extension 18 between a tube end and the patient tube connector. The method also includes separating the tube end from the patient tube connector by continuing to push the extension tip within the gap formed between the tube end and the patient tube connector such that as the extension tip continues to move further within the gap, the ramped surface (increasing in thickness moving from an extension tip towards the operator end) of each extension facilitates the smooth separation of the patient tube connector from a tube end or a tube end connector. The method can further include engaging a separated patient tube connector with elevated ridge 24 of extensions 18 such that the separated patient tube connector is held or supported therein.

Figure 7:
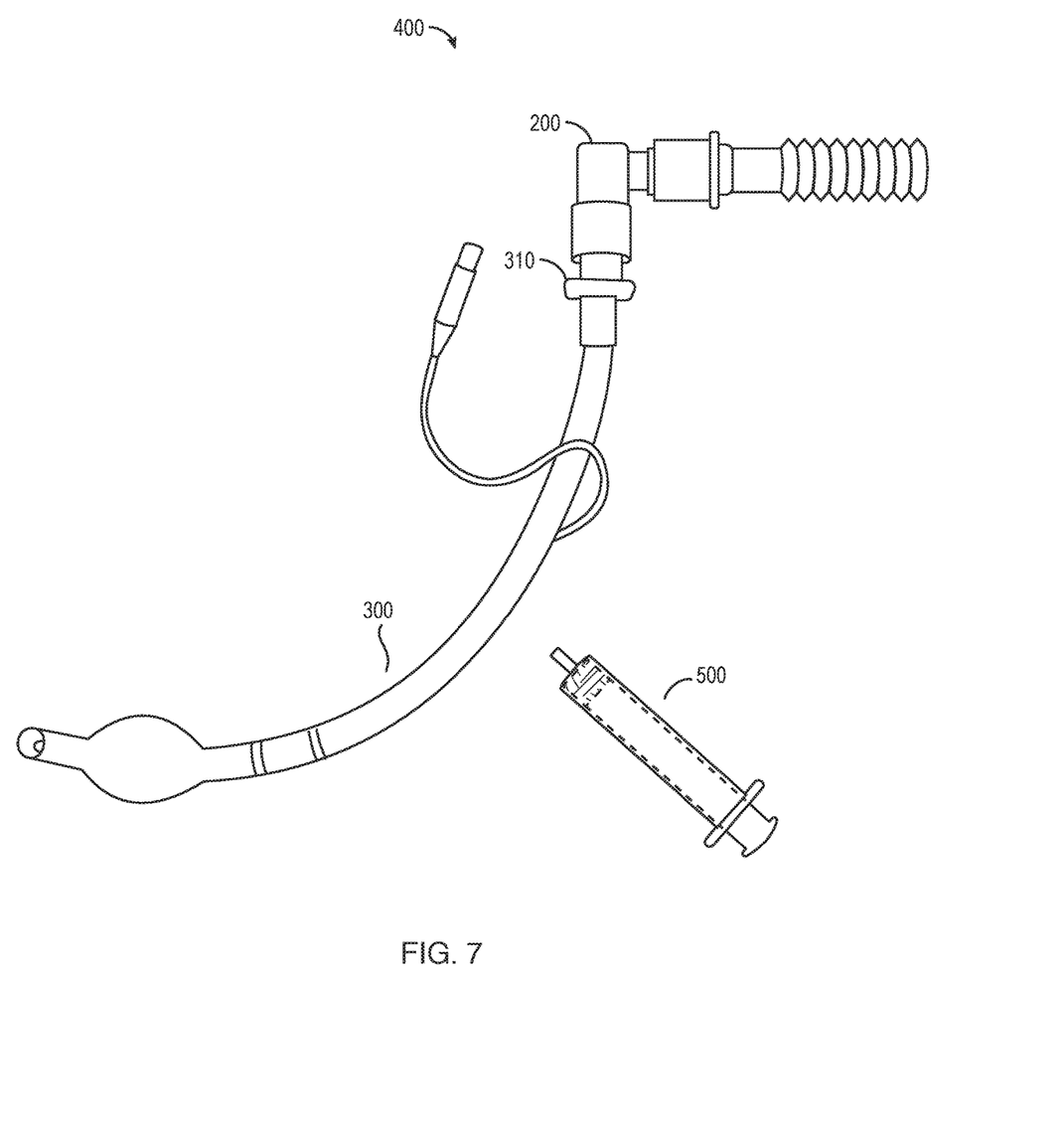
FIG. 7 is a perspective view of an endotracheal tube device with which the clamping forceps device can be used, according to one or more embodiments of the presently disclosed subject matter.

FIG. 7 is a perspective view of an endotracheal tube device 400. The clamping forceps device as disclosed herein can be used to occluding tube 300 of endotracheal tube device 400 as well as for separating patient tube connector 200 of endotracheal tube device 400, according to one or more embodiments of the presently disclosed subject matter. FIG. 7 further illustrates a syringe 500.

While existing state of the art discloses various clamping forceps, they fail to teach a clamping forceps with a wedging mechanism incorporated within (or built into) the clamping forceps that can be advantageously used to disconnect the patient tube connector from an end of the oxygen supply tube in an expeditious fashion.

By contrast, the clamping forceps as discloses herein advantageously includes a built-in wedge mechanism that is easily accessible to medical professional so that unnecessary delay associated with disconnecting a patient tube connector from an end of the oxygen supply tube can be avoided by the use of wedge mechanism built into the clamping forceps. Embodiments of the presently disclosed subject matter can also operate to minimize or eliminate the inconvenience that a patient may be subjected to during the separation of the patient tube connector (in fluid communication with a patient's trachea) from a tube supplying a fluid (e.g., a gas) under previously known methods. With the approximate u-shape of the disconnecting wedge mechanism providing for a cradle to support the patient tube connector being disconnected, the patient is not subjected to undesirable jerks that can result from previously known methods of separating the patient tube connector from an end connection of the tube supplying a fluid. After the patient tube connector is separated from an end of the fluid supply tube, the patient tube connector can be connected to the end of a tube supplying fluid from a new source such as, for example, a new oxygen cylinder.

It should be noted that whereas the embodiments of the presently disclosed subject matter have been described in relation to a patient tube connector in fluid communication with the trachea of a patient, the invention is not necessarily limited to only such or similar uses. Embodiments of the presently disclosed subject matter can also be used in any applications wherein it would be beneficial to provide a pair of clamping forceps that includes a disconnecting wedge mechanism for separating a flexible conduit from a joint or coupling.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of using a clamping forceps device, the method comprising:
   providing a clamping forceps device, the clamping forceps device comprising:
      two clamps in pivotal connection to one another and each having an operator end for being operated by a health care provider; and,
      an extension extending aft of the operator end of each clamp, the extension forming a space therebetween sized to form a disconnecting wedge mechanism for separating a tube from a patient tube connector, wherein each extension defines a ramped surface increasing in thickness moving from an extension tip towards the operator end;
   inserting an extension tip of each extension between a tube end and the patient tube connector; and
   separating the tube end from the patient tube connector.

2. The method of claim 1, wherein each extension incudes an elevated ridge at a side facing the other extension, wherein the method further comprises engaging a separated patient tube connector with the elevated ridges.

* * * * *